US010751075B2

(12) United States Patent
Merza et al.

(10) Patent No.: US 10,751,075 B2
(45) Date of Patent: Aug. 25, 2020

(54) DEVICE FOR AXIAL ATTACHMENT AND RADIAL DETACHMENT OF DISPOSABLE BLADES

(71) Applicant: Gyrus ACMI, Inc., Southborough, MA (US)

(72) Inventors: Saeed A. Merza, Cordova, TN (US); Joey Magno, Cordova, TN (US)

(73) Assignee: Gyrus ACMI, Inc., Southborough, MA (US)

( * ) Notice: Subject to any disclaimer, the term of this patent is extended or adjusted under 35 U.S.C. 154(b) by 164 days.

(21) Appl. No.: 15/822,554

(22) Filed: Nov. 27, 2017

(65) Prior Publication Data

US 2018/0146972 A1     May 31, 2018

Related U.S. Application Data

(60) Provisional application No. 62/427,899, filed on Nov. 30, 2016.

(51) Int. Cl.
*A61B 17/32*     (2006.01)
*A61B 17/00*     (2006.01)
*F16B 7/20*      (2006.01)

(52) U.S. Cl.
CPC ........ *A61B 17/32* (2013.01); *A61B 17/32002* (2013.01); *A61B 2017/0046* (2013.01); *A61B 2017/00473* (2013.01); *A61B 2017/00477* (2013.01); *F16B 7/20* (2013.01)

(58) Field of Classification Search
CPC .............. A61B 17/32; A61B 17/32002; A61B 2017/0046; A61B 2017/00473; A61B 2017/00477
See application file for complete search history.

(56) References Cited

U.S. PATENT DOCUMENTS

| 5,888,200 | A | * | 3/1999 | Walen | ................ | A61B 17/1622 606/167 |
|---|---|---|---|---|---|---|
| 8,075,551 | B2 | | 12/2011 | Eberle | | |
| 8,353,622 | B2 | | 1/2013 | Henniges et al. | | |
| 8,540,745 | B2 | * | 9/2013 | Criscuolo | .......... | A61B 17/0218 606/190 |
| 2008/0157488 | A1 | | 7/2008 | Kullmer et al. | | |
| 2017/0135715 | A1 | * | 5/2017 | Breindel | ............ | A61B 17/3209 |

* cited by examiner

*Primary Examiner* — Diane D Yabut
(74) *Attorney, Agent, or Firm* — Harrington & Smith

(57) ABSTRACT

Disclosed herein is a medical apparatus. The medical apparatus includes an adapter, a tool hub, and a releasing member. The adapter is configured to be fastened to a surgical handpiece. The adapter has a lumen, and the lumen has an interior surface. The tool hub is configured to be fastened to the adapter by a snap-in mechanism through the interior surface of the lumen. The releasing member is configured to release the tool hub from the adapter by a twisting force on the releasing member. The releasing member includes a restoring mechanism configured to restore the releasing member from a twisted state to a normal standing state upon removal of the twisting force.

20 Claims, 9 Drawing Sheets

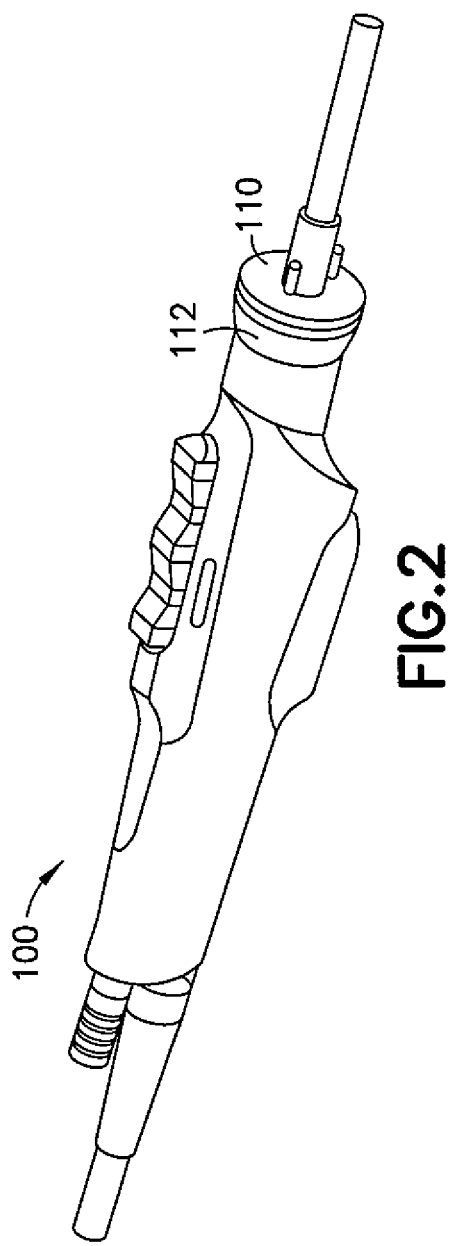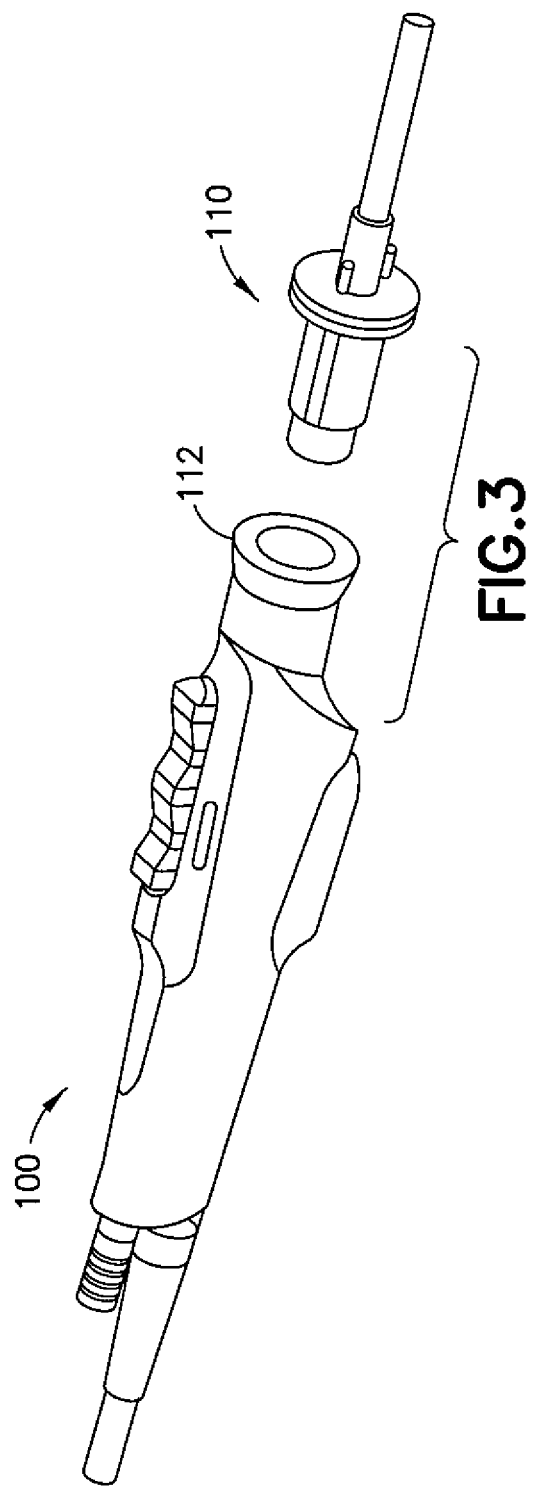

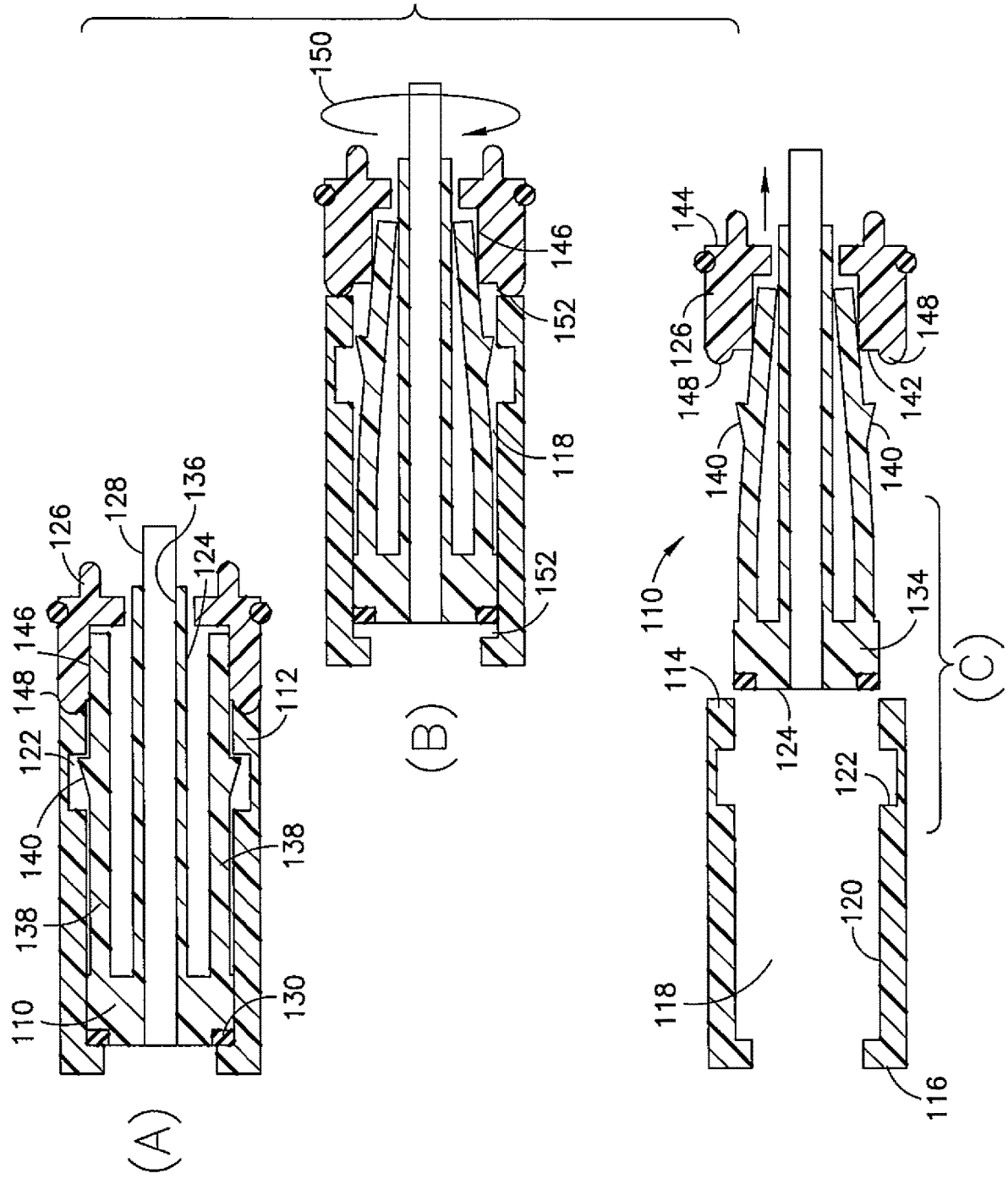

DEVICE FOR AXIAL ATTACHMENT AND RADIAL DETACHMENT OF DISPOSABLE BLADES

CROSS REFERENCE TO RELATED APPLICATION

This application claims priority under 35 U.S.C. § 119(e) to U.S. provisional patent application No. 62/427,899 filed Nov. 30, 2016, which is hereby incorporated by reference in its entirety.

BACKGROUND

Field of the Invention

The invention relates to medical shaver devices, and more specifically relates to attachments for medical shaver devices.

Brief Description of Prior Developments

Orthopedics and ENT medical shaver devices use disposable blades as attachments. Securing disposable blades inside a handpiece is generally a required feature and can play an important role in shaving performance. One of the most common methods is snap-in latches. FIG. 1 illustrates a conventional medical shaver device having a disposable blade hub assembly with snap-in latches. The snap-in latch configuration provides for a snap latch press and release method to attach and detach blades from a handpiece shaver. Referring now to portion (A) of FIG. 1, the disposable blade hub assembly 10 comprises a snap latch 12 and is attached to handpiece blade adapter 14 and secured by a protrusion 16 on the snap latch 12 which extends into an internal groove or slot 18 of the handpiece blade adapter 14. The disposable blade hub assembly 10 further comprises a snap latch push release 20, a blade tube 22, a blade hub 24, and a seal 26. In portion (B) of FIG. 1, the snap latch push release 20 is pressed to allow the blade hub assembly to release (unlatch), such that the snap latch deflects inwardly and disengages the protrusion 16 from the slot 18. In portion (C) of FIG. 1, the blade hub assembly 10 is pulled out from handpiece shaver adapter 14.

Conventional snap-in latch configurations (as shown in FIG. 1) are generally reliable and not costly to fabricate. However, in order to release the disposable blade hub assembly from the handpiece, a bending of the snap latch is generally required. The force required to bend the snap latch is usually generated by pressing into the latch with the user's index finger and/or with a thumb if it's a double latch design (as shown in portion [B] of FIG. 1). Disposable blade designs also generally include the rubber seal to prevent leakage though the attachment gap to allow for suction aspiration. However, the rubber seal(s) on the outside diameter of the blade hub often get stuck or adhere to the blade adapter inside diameter of the hand piece which complicates the detachment process. The user will then generally require a certain pulling force to release the blade out to overcome the friction of the seals while maintaining pressure on the snap latch with his or her finger(s) which might be ergonomically difficult to do.

Accordingly, as the conventional designs generally result in various limitations and disadvantages (as described above), there is a need to provide improved and reliable product configurations.

SUMMARY

In accordance with one aspect of the invention, a medical apparatus is disclosed. The medical apparatus includes an adapter, a tool hub, and a releasing member. The adapter is configured to be fastened to a surgical handpiece. The adapter has a lumen, and the lumen has an interior surface. The tool hub is configured to be fastened to the adapter by a snap-in mechanism through the interior surface of the lumen. The releasing member is configured to release the tool hub from the adapter by a twisting force on the releasing member. The releasing member includes a restoring mechanism configured to restore the releasing member from a twisted state to a normal standing state upon removal of the twisting force.

In accordance with another aspect of the invention, a medical apparatus is disclosed. The medical apparatus includes a surgical handpiece, an adapter, a tool hub, and a releasing member. The surgical handpiece has a receiving end. The adapter is configured to be fastened to the receiving end of the surgical handpiece. The adapter has a lumen, and the lumen has an interior surface. The tool hub is configured to be fastened to the adapter by a snap-in mechanism through the interior surface of the lumen. The tool hub is capable of holding a surgical tool. The releasing member is configured to release the tool hub from the adapter by a twisting force on the releasing member.

In accordance with another aspect of the invention, a medical apparatus is disclosed. The medical apparatus includes a surgical handpiece, an adapter, a tool hub, and a releasing member. The surgical handpiece has a receiving end. The adapter is configured to be fastened to the receiving end of the surgical handpiece. The adapter has a lumen, and the lumen has an interior surface. The tool hub is configured to be fastened to the adapter by a snap-in mechanism through the interior surface of the lumen. The releasing member is configured to release the tool hub from the adapter by a twisting force on the releasing member. The releasing member includes a restoring mechanism configured to restore the releasing member from its twisted state to its normal standing state upon removal of the twisting force.

BRIEF DESCRIPTION OF THE DRAWINGS

The foregoing aspects and other features of the invention are explained in the following description, taken in connection with the accompanying drawings, wherein:

FIG. 2 is a perspective view of a medical shaver handpiece incorporating features of the invention;

FIG. 3 is an exploded perspective view of the medical shaver handpiece shown in FIG. 2;

FIG. 4 provides various section views of portions of the medical shaver handpiece shown in FIG. 2;

DETAILED DESCRIPTION

Figure 1:
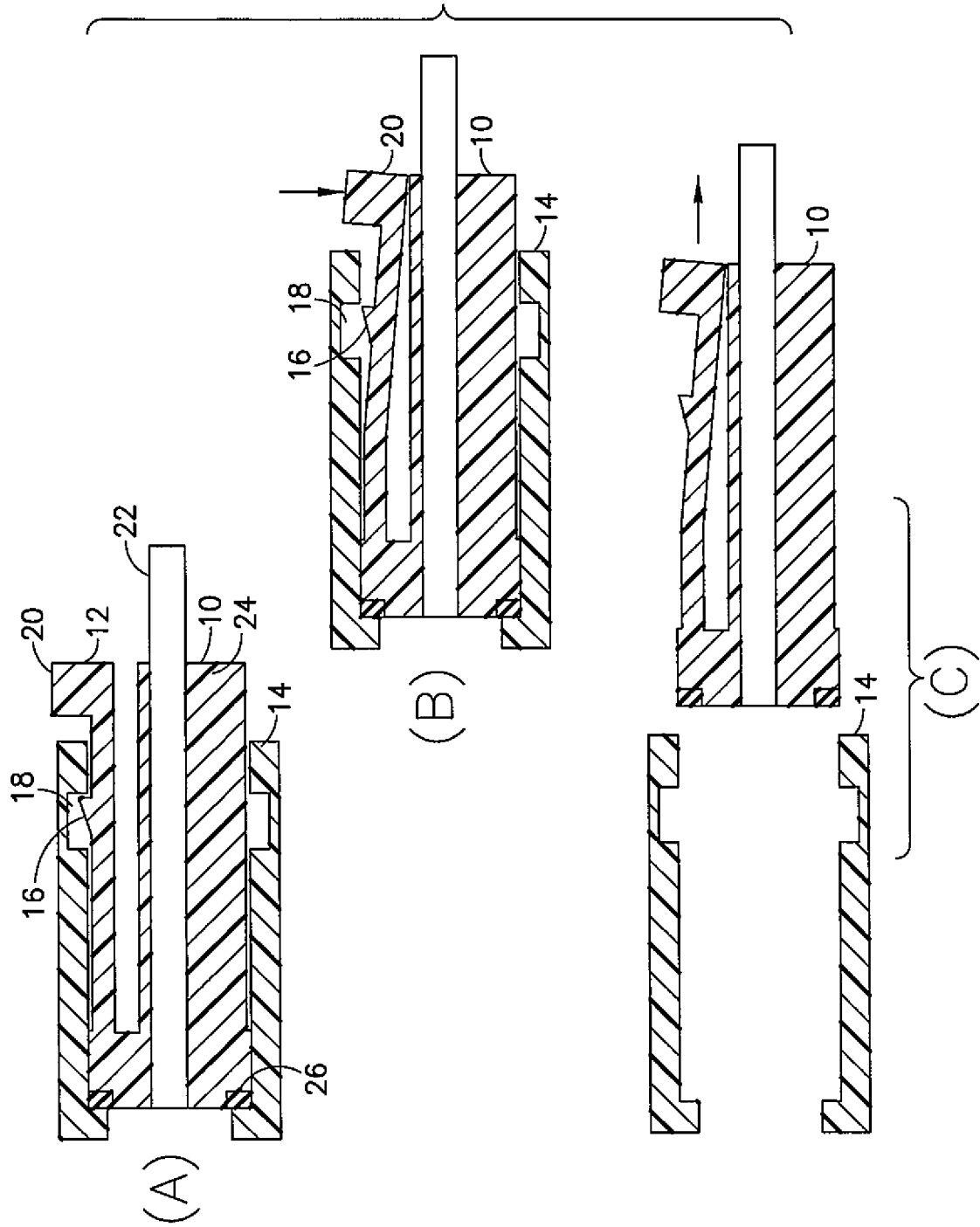
FIG. 1 is a section view of a conventional disposable blade and handpiece blade adapter.

Referring to FIGS. 2 and 3, there is shown a perspective view of a medical shaver handpiece 100 with a disposable blade hub assembly 110 and blade adapter 112 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

The handpiece blade adapter 112 comprises a general tubular or cylindrical configuration and is connected to a receiving end of the handpiece 100. According to some embodiments of the invention, the blade adapter 112 is configured to be removably attached (or detachable) to (or from) the end of the handpiece 100. According to some other embodiments, the blade adapter 112 is fixably attached (or fastened) to the end of the handpiece 100. As shown in FIG. 3 the disposable blade hub assembly 110 is removably attached (or detachable) to (or from) the blade adapter 112.

Referring now also to FIG. 4, there is shown a section view of the disposable blade hub assembly 110 and the handpiece blade adapter 112. The blade adapter 112 comprises a first end 114 and a second end 116 and a lumen (or central cavity) 118 which extends between the first end 114 and the second end 116. The lumen 118 has an interior surface 120. According to various exemplary embodiments, the interior surface may comprise a groove or slot 122. The disposable blade hub assembly 110 comprises a blade hub 124 and a releasing member (or twist release) 126. The disposable blade hub assembly 110 further comprises a blade tube 128, a seal 130, and an O-ring 132. The blade tube 128 is configured to be received by a central portion on the blade hub 124 (or tool hub). The seal 130 is configured to be disposed between the blade hub 124 and the second end 116 of the blade adapter 112. The O-ring 132 is generally disposed at an outer circumference of the releasing member 126.

The blade hub 124 comprises a base portion 134, a central cavity 136, and snap latches 138. The central cavity 136 extends from the base portion 134 and is configured to receive the blade tube 128. The snap latches 138 extend from the base portion 134 and are configured to be engageable with the interior surface 120 of the lumen 118 of the blade adapter 112. According to various exemplary embodiments of the invention, the snap latches 138 are engageable with the interior surface 120 via a snap-in mechanism. The snap-in mechanism may comprise a protrusion 140 on each of the snap latches 138 which is configured to extend into the slot 122 of the internal surface 120. It should be noted that although the protrusions 140 are illustrated as having a general ramp shape, any suitable shape or configuration may be provided.

The releasing member (or twist release) 126 comprises a first end 142, a second end 144, and an interior portion 146. The first end 142 comprises pinhead portions 148 configured to contact the first end of the blade adapter 112. The second end 144 is opposite the first end 142. The interior portion 146 is configured to be engageable with ends of the snap latches 138. According to various exemplary embodiments the releasing member may be attached or secured to the blade hub by a snap fit feature, however in alternate embodiments, any suitable attachment configuration may be provided.

Portions (A), (B), and (C) of FIG. 4 illustrate an exemplary process of detaching the blade hub assembly (or blades) from the shaver handpiece. For example, portion (A) shows the blade hub assembly 110 installed in the handpiece blade adapter 112 with the protrusions 140 snapped-in, or engaged with, the slot 122. Portion (B) shows a twisting direction 150 to be applied to the releasing member 126 to twist to unlatch the snap latches 138 from the interior surface 120 of the blade adapter 112, such that the snap latches deflect inwardly and disengages the protrusions 140 from the slot 122. The deflection of the snap latches 138 is provided by engagement of the ends of the snap latches 138 with the interior portion 146 of the releasing member 126 (which will be described in detail below). The twisting (or rotating) of the releasing member provides for an initial self detachment at areas 152. In portion (C) of FIG. 4, the blade hub assembly 110 is pulled out from handpiece shaver adapter 112 to extract the blade from the adapter.

Various exemplary embodiments of the invention help eliminate the need for the intensive snap latch push and blade pull (as in the prior art). Various features of the exemplary embodiments permit the user to twist the blade release mechanism while it is engaged inside the blade adapter and allow the said mechanism to release the latch and extract itself out. This method is ergonomic since it will reduce the effort of the user to use any intensive pull force to detach blades from the shaver handpiece.

Figure 5:
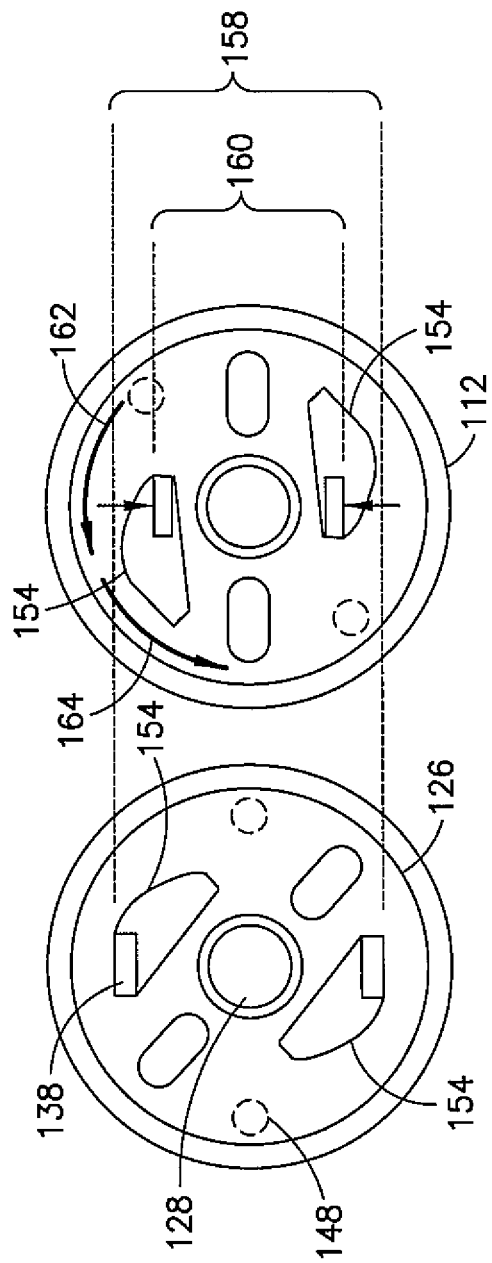
FIG. 5 illustrates front section views of a blade hub assembly of the medical shaver handpiece shown in FIG. 2.
Figure 6:
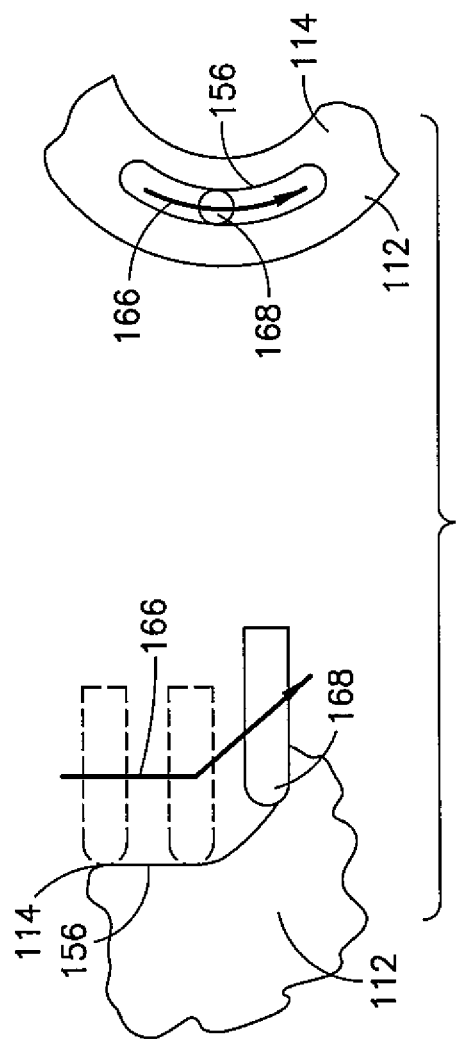
FIG. 6 illustrates side and front views of portions of the blade adapter and the twist release part of the medical shaver handpiece shown in FIG. 2.

As shown in FIG. 4, the disposable blade hub assembly generally comprises a stationary part (the blade hub 124) and a moving part (the releasing member 126). Referring now to FIGS. 5 and 6, first cam features 154 and second cam features 156 are provided to release the latches 138 and detach the blade from the handpiece. The first cam features 154 are at the interior portion 146 of the twist release part 126 which provides the necessary bending of the snap latches 138 to release from the latch (see dashed lines 158 for a 'Snap Actuated' position and dashed lines 160 for a 'Snap Released' position). In addition, the blade adapter 112 comprises the second cam features 156 which enables blade extraction (see FIG. 6). The pinheads 148 of the twist release part 126 move along the cam profile of cam features 156 to enable the latch release and blade extraction in two steps. First, by twisting the twist release part (see arrow 162), the end of the latches 138 are pressed though the cam profile of the first cam features 154 allowing the latches to release. Second, continuing twisting the twist release part 126 (see arrow 164) allows the whole blade assembly to detach itself from the shaver handpiece blade adapter. As shown in FIG. 6, the cam profile of the second cam features 156 (of the blade adapter of the handpiece) has a straight path (to permit the first step twist [see pinhead motion at 166]) and an angled path (to permit the second twist step [see pinhead location 168]).

After releasing the blade hub assembly 110 from the handpiece, it may be required to have the twisting part 126 returned to its original location/position so it can be ready for the next re-attachment. This returning feature could be achieved without user effort. Therefore, either of the embodiments introduced below will be sufficient to untwist or return the twist release part back to its own location/position after releasing the blade from the shaver.

Figure 7:
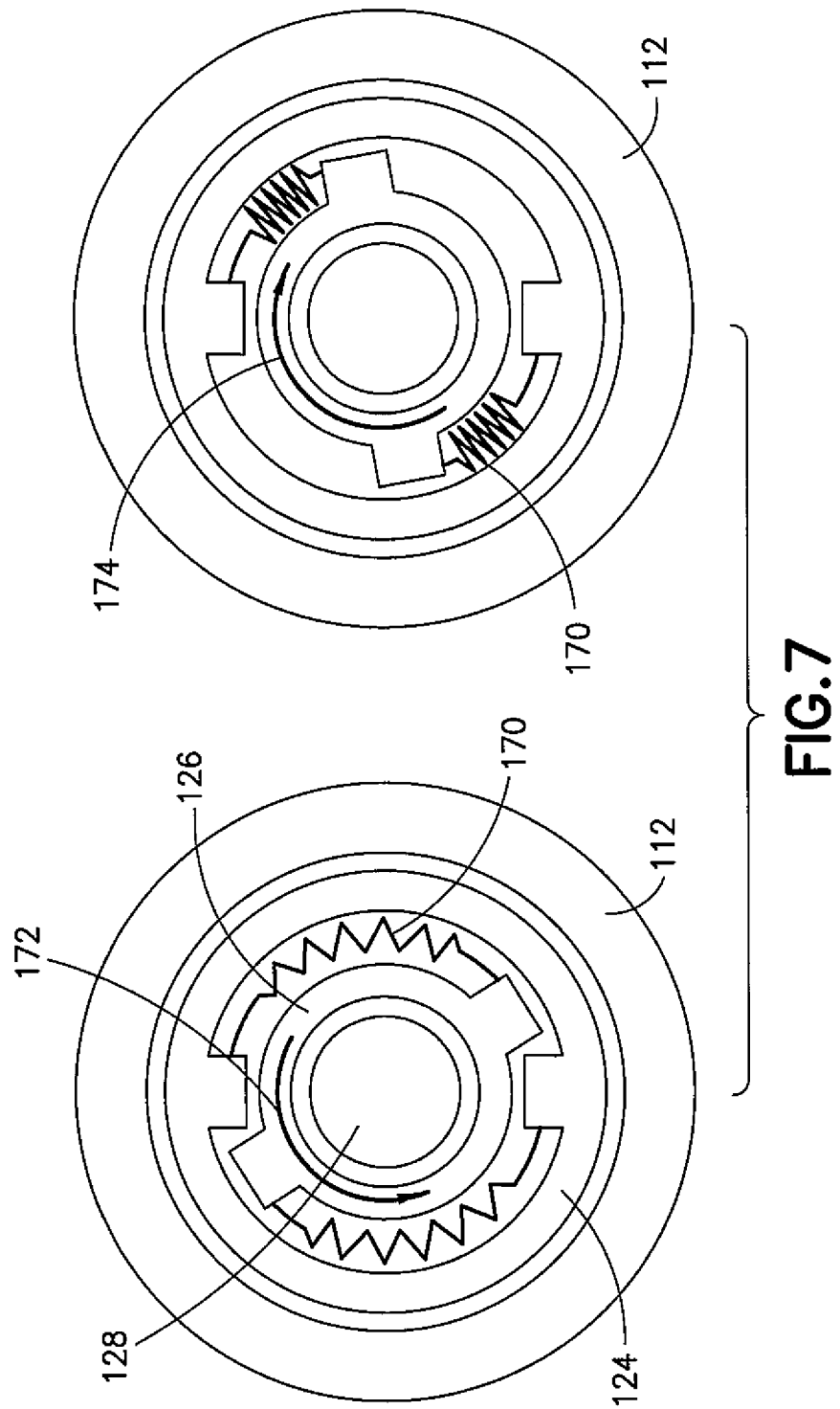
FIG. 7 shows front section views of portions of the blade adapter, the blade hub, and the twist release part of the medical shaver handpiece shown in FIG. 2 corresponding to a returning feature.

According to one embodiment, and referring to FIG. 7, a torsion spring configuration is disclosed. For example, torsion compression springs 170 are provided between the blade hub 124 and the twist release part 126. The twist release part (or releasing member) 126 is returned to its initial location/position through (a biasing force of) the torsion spring(s) 170. As shown in FIG. 7, arrow 172 illustrates the direction of rotation of the releasing member 126 to release the snap latches, and arrow 174 illustrates the direction of rotation to return back to original position.

Figure 8:
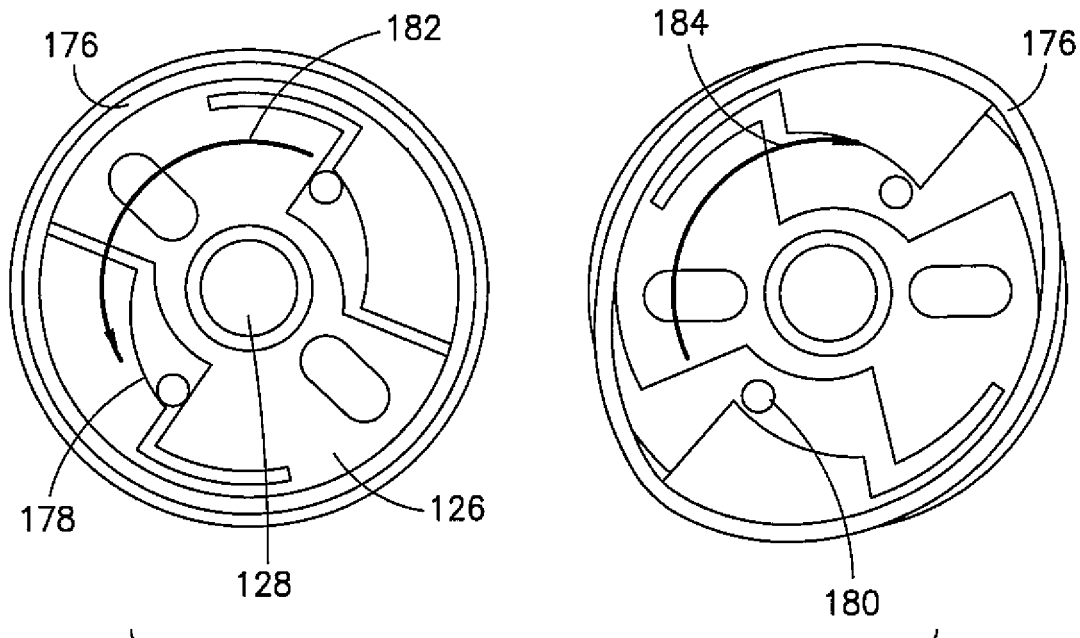
FIG. 8 is shows front section views of portions of the blade hub and the twist release part of the medical shaver handpiece shown in FIG. 2 corresponding to another embodiment of a returning feature.

According to another embodiment, and referring to FIGS. 8-11, an O-ring configuration is disclosed. For example, an O-ring 176 can be placed around the twist release part 126. In order for the O-ring 176 to generate the force for the twist release part to return to its initial place, a cam profile 178 is provided at the twist release part 126 which is configured to engage a blade hub pin 180. The profile 178 allows for change in shape of the twist release part as the user twists it. The initial location of the twist release part has a smaller perimeter length than its fully twisted part. Therefore, the O-ring 176 will provide the necessary force to return the twist release part to its initial location. This is achieved because of the expansion of twist release part and the tension of the O-ring. As shown in FIG. 8, arrow 162 illustrates the direction of rotation of the releasing member 126 to release the snap latches, and arrow 184 illustrates the direction of rotation to return back to original position.

Figure 9:
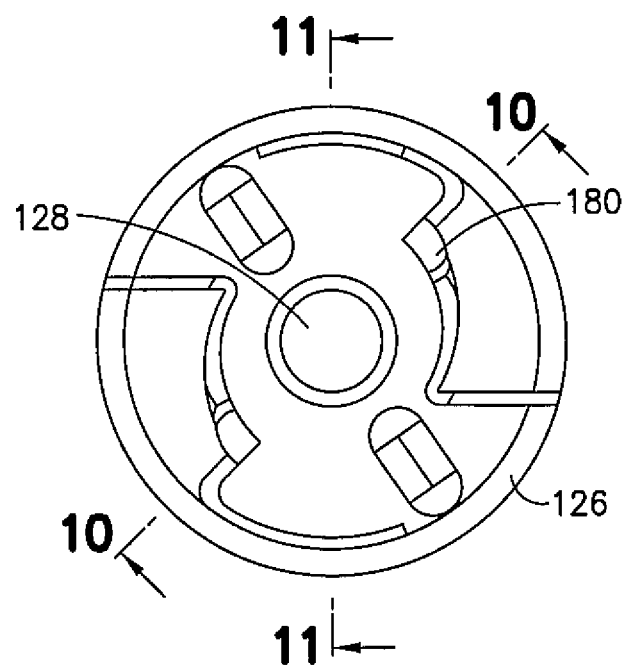
FIG. 9 is a front view of the twist release part showing section lines corresponding to FIGS. 10, 11.
Figure 10:
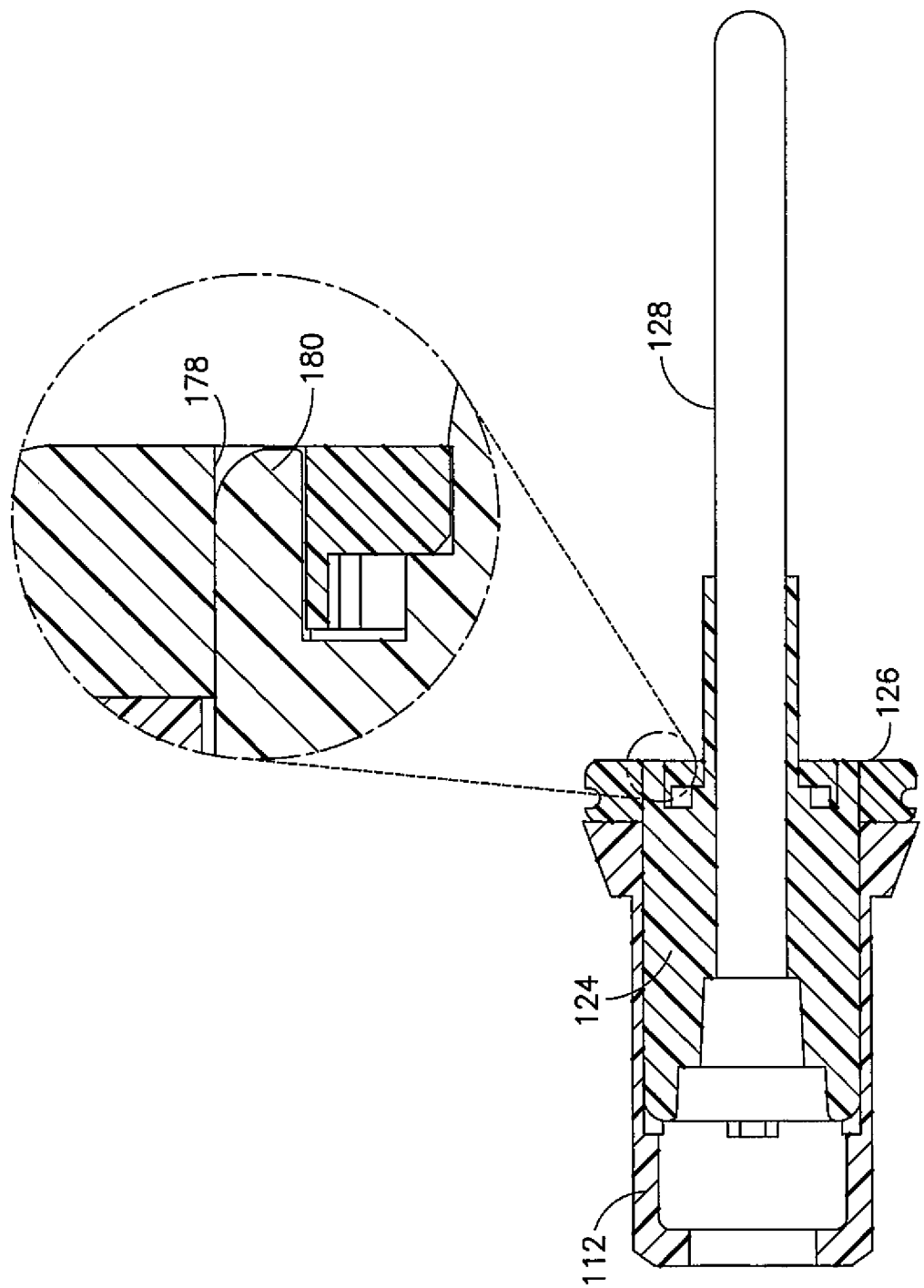
FIG. 10 is a section view and enlarged section view taken along line 10-10 in FIG. 9.
Figure 11:
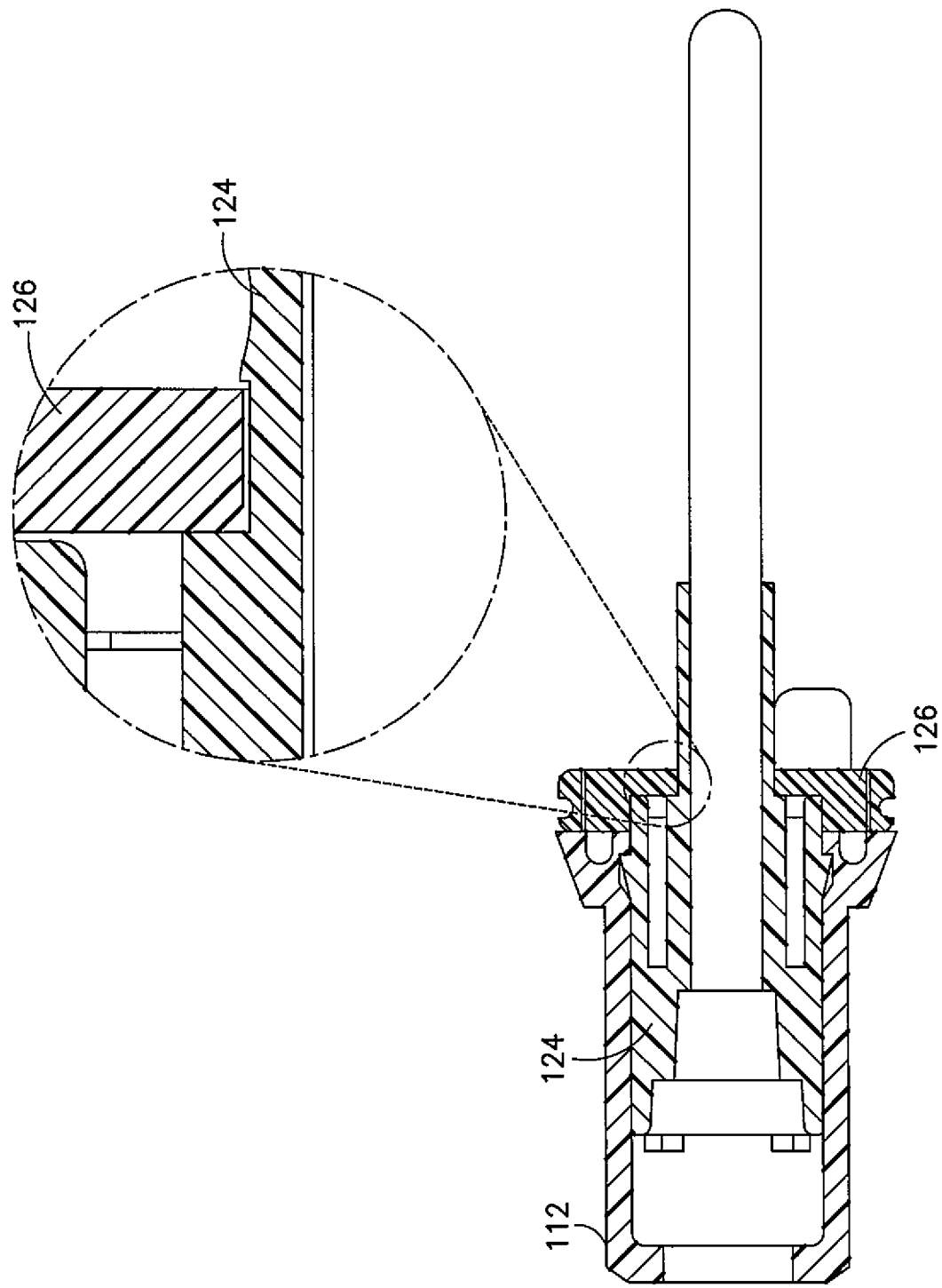
FIG. 11 is a section view and enlarged section view taken along line 11-11 in FIG. 9.
Figure 12:
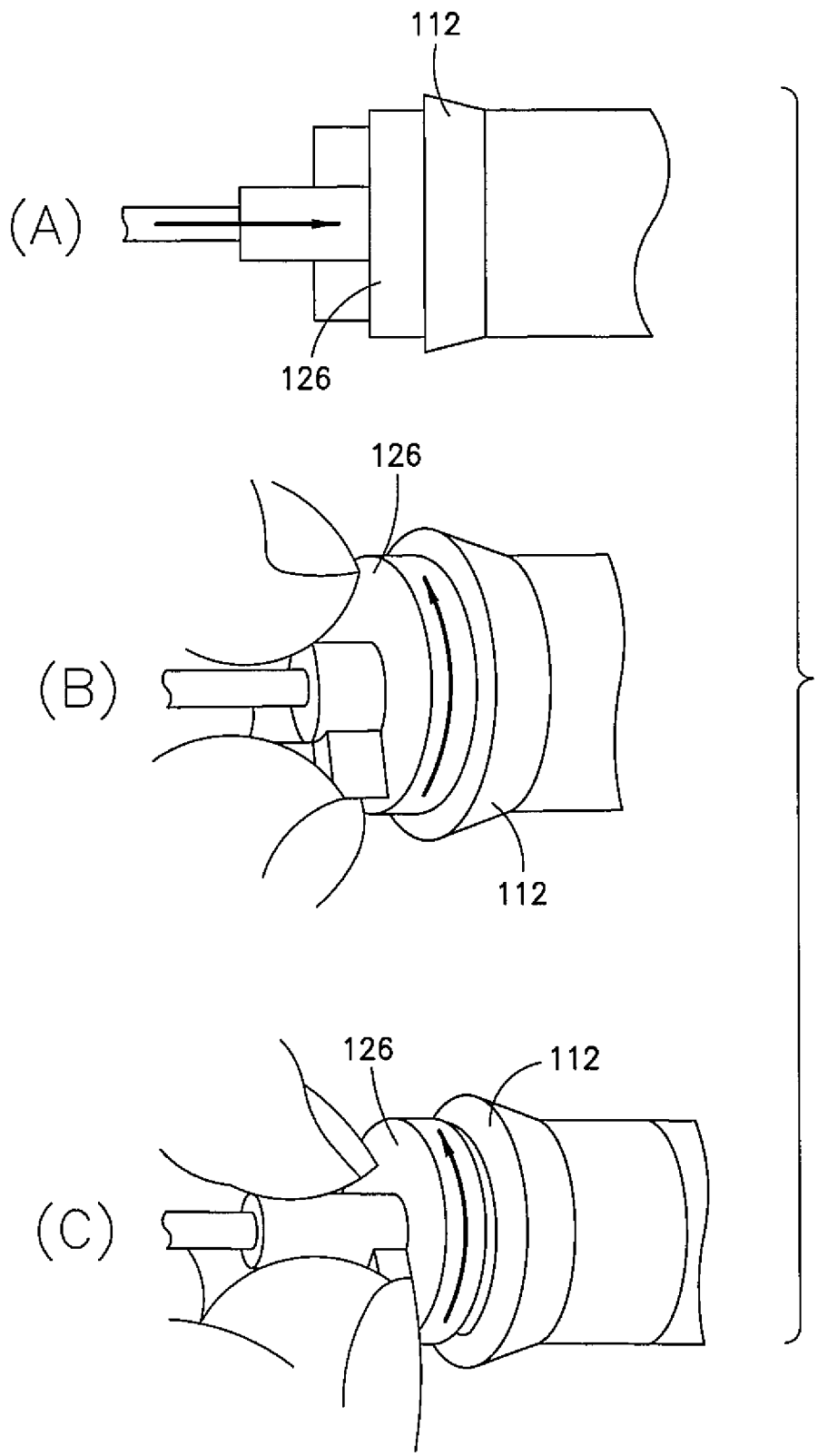
FIG. 12 provides various perspective views of portions of the blade adapter and the twist release part of the medical shaver handpiece shown in FIG. 2.

FIG. 9 illustrates section lines 10-10 and 11-11 which correspond to the section views of FIGS. 10, 11, respectively. FIG. 11 illustrates a section view of the blade hub pin 180 and the cam profile 178 of the twist release part 126. FIG. 12 illustrates a snap fit feature which secures/fastens the releasing member 126 to the blade hub 124. However, it should be noted that in alternate embodiments, any suitable attachment configuration may be provided.

Referring now to FIG. 12, an exemplary embodiment of the twist and release function and detachment is illustrated. It should be noted that the self-returning mechanism is not shown in FIG. 12. Portion (A) of FIG. 12 shows the blade with axial insert, wherein the blade is inserted axially and secured with the snap latch. Portion (B) of FIG. 12 shows the twist to release snaps, wherein the first step twist (about 25 degree twist angle) to release the latches. Portion (C) of FIG. 12 shows the continued twist to eject blade, wherein the continued twisting (about additional 25 degree twist angle) to eject the blade.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a medical apparatus is disclosed. The medical apparatus comprises: an adapter configured to be fastened to a surgical handpiece, the adapter having a lumen, and the lumen having an interior surface; a tool hub configured to be fastened to the adapter by a snap-in mechanism through the interior surface of the lumen; and a releasing member configured to release the tool hub from the adapter by a twisting force on the releasing member, the releasing member comprising a restoring mechanism configured to restore the releasing member from a twisted state to a normal standing state upon removal of the twisting force.

A medical apparatus as above, wherein the releasing member comprises a cam feature.

A medical apparatus as above, wherein the twisting force on the releasing member is configured to rotate the cam feature.

A medical apparatus as above, wherein an end of the adapter comprises a cam feature, wherein the cam feature is adjacent the releasing member.

A medical apparatus as above, wherein the restoring mechanism comprises a spring or an O-ring.

In another exemplary embodiment, a medical apparatus is disclosed. The medical apparatus comprises: a surgical handpiece having a receiving end; an adapter configured to be fastened to the receiving end of the surgical handpiece, the adapter having a lumen, and the lumen having an interior surface; a tool hub configured to be fastened to the adapter by a snap-in mechanism through the interior surface of the lumen, the tool hub capable of holding a surgical tool; and a releasing member configured to release the tool hub from the adapter by a twisting force on the releasing member.

A medical apparatus as above, wherein the releasing member comprises a cam feature.

A medical apparatus as above, wherein the twisting force on the releasing member is configured to rotate the cam feature.

A medical apparatus as above, wherein an end of the adapter comprises a cam feature, wherein the cam feature is adjacent the releasing member.

A medical apparatus as above, further comprising a restoring mechanism configured to restore the releasing member from a twisted state to a normal standing state upon removal of the twisting force.

In another exemplary embodiment, a medical apparatus is disclosed. The medical apparatus comprises: a surgical handpiece having a receiving end; an adapter configured to be fastened to the receiving end of the surgical handpiece, the adapter having a lumen, and the lumen having an interior surface; a tool hub configured to be fastened to the adapter by a snap-in mechanism through the interior surface of the lumen; and a releasing member configured to release the tool hub from the adapter by a twisting force on the releasing member, the releasing member comprising a restoring mechanism configured to restore the releasing member from its twisted state to its normal standing state upon removal of the twisting force.

A medical apparatus as above, wherein the releasing member comprises a cam feature.

A medical apparatus as above, wherein the twisting force on the releasing member is configured to rotate the cam feature.

A medical apparatus as above, wherein an end of the adapter comprises a cam feature, wherein the cam feature is adjacent the releasing member.

A medical apparatus as above, wherein the restoring mechanism comprises a spring or an O-ring.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A medical apparatus, comprising:
an adapter configured to be fastened to a surgical handpiece, the adapter having a lumen, and the lumen having an interior surface;
a tool hub configured to be releasably fastened to the adapter by a snap-in mechanism at the interior surface of the lumen; and
a releasing member configured to release the tool hub from the adapter by a twisting force on the releasing member, where the releasing member receives an end of the tool hub and is movably connected thereto, where the releasing member comprises a restoring mechanism coupled to the tool hub and is configured to restore the releasing member from a twisted state to a normal standing state upon removal of the twisting force, and where the restoring mechanism comprises a biasing member configured to bias the releasing member relative to the tool hub towards the normal standing state.

2. A medical apparatus as in claim 1 wherein the releasing member comprises a cam feature.

3. A medical apparatus as in claim 2 wherein the twisting force on the releasing member is configured to rotate the cam feature.

4. A medical apparatus as in claim 1 wherein an end of the adapter comprises a cam feature, wherein the cam feature is adjacent the releasing member.

5. A medical apparatus as in claim 1 wherein the restoring mechanism comprises a spring or an O-ring.

6. A medical apparatus as in claim 1 wherein the releasing member is configured to be slid onto the tool hub.

7. A medical apparatus as in claim 1 wherein the releasing member is configured to be placed onto the tool hub after the tool hub is connected to the adapter.

8. A medical apparatus as in claim 1 wherein the snap-in mechanism comprises at least two opposite deflectable cantilevered arms on the tool hub.

9. A medical apparatus, comprising:
a surgical handpiece having a receiving end;
an adapter configured to be fastened to the receiving end of the surgical handpiece, the adapter having a lumen, and the lumen having an interior surface;
a tool hub configured to be releasably fastened to the adapter by a snap-in mechanism of the tool hub that engages the interior surface of the lumen, the tool hub capable of holding a surgical tool; and
a releasing member configured to release the tool hub from the adapter by a twisting force on the releasing member, where the releasing member is configured to removably attach to the tool hub, and where the releasing member is configured to deflect a portion of the tool hub to unlatch the snap-in mechanism.

10. A medical apparatus as in claim 9 wherein the releasing member comprises a cam feature.

11. A medical apparatus as in claim 10 wherein the twisting force on the releasing member is configured to rotate the cam feature.

12. A medical apparatus as in claim 9 wherein an end of the adapter comprises a cam feature, wherein the cam feature is adjacent the releasing member.

13. A medical apparatus as in claim 9 further comprising a restoring mechanism comprising a biasing member configured to restore the releasing member from a twisted state to a normal standing state upon removal of the twisting force.

14. A medical apparatus as in claim 9 wherein the releasing member is configured to be slid onto the tool hub.

15. A medical apparatus as in claim 9 wherein the releasing member is configured to be placed onto the tool hub after the tool hub is connected to the adapter.

16. A medical apparatus, comprising:
a surgical handpiece having a receiving end;
an adapter configured to be fastened to the receiving end of the surgical handpiece, the adapter having a lumen, and the lumen having an interior surface;
a tool hub configured to be releasably fastened to the adapter by a snap-in mechanism of the tool hub at the interior surface of the lumen; and
a releasing member configured to release the tool hub from the adapter by a twisting force on the releasing member, where the releasing member is movably connected to the tool hub, where the releasing member is configured to removably attach to the tool hub, and where the releasing member is configured to deflect a portion of the tool hub to unlatch the snap-in mechanism, where the releasing member comprises a restoring mechanism configured to restore the releasing member from a twisted state to a normal standing state upon removal of the twisting force, and where the restoring mechanism comprises a biasing member configured to bias the releasing member from the tool hub to the normal standing state.

17. A medical apparatus as in claim 16 wherein the releasing member comprises a cam feature.

18. A medical apparatus as in claim 17 wherein the twisting force on the releasing member is configured to rotate the cam feature.

19. A medical apparatus as in claim 16 wherein an end of the adapter comprises a cam feature, wherein the cam feature is adjacent the releasing member.

20. A medical apparatus as in claim 16 wherein the restoring mechanism comprises a spring or an O-ring.

* * * * *